United States Patent
Morris et al.

(10) Patent No.: US 7,150,724 B2
(45) Date of Patent: Dec. 19, 2006

(54) SYRINGE PLUNGER DRIVER SYSTEM

(75) Inventors: Matthew G. Morris, San Diego, CA (US); Spyros Kasvikis, Escondido, CA (US); Donald F. Schwartz, San Diego, CA (US)

(73) Assignee: Cardinal Health 303, Inc., San Diego, CA (US)

( * ) Notice: Subject to any disclaimer, the term of this patent is extended or adjusted under 35 U.S.C. 154(b) by 0 days.

(21) Appl. No.: 10/164,112

(22) Filed: Jun. 5, 2002

(65) Prior Publication Data
US 2003/0229311 A1  Dec. 11, 2003

(51) Int. Cl.
*A61M 37/00* (2006.01)
(52) U.S. Cl. ..................................... 604/131
(58) Field of Classification Search .............. 604/65, 604/67, 151, 155, 246, 152, 154, 131, 134; 125/DIG. 1, DIG. 12, DIG. 13
See application file for complete search history.

(56) References Cited

U.S. PATENT DOCUMENTS

| | | | |
|---|---|---|---|
| 4,838,857 A | 6/1989 | Strowe et al. | 604/67 |
| 5,034,004 A | 7/1991 | Crankshaw | 604/154 |
| 5,242,408 A * | 9/1993 | Jhuboo et al. | 604/152 |
| 5,501,665 A | 3/1996 | Jhuboo et al. | 604/65 |
| 5,545,140 A * | 8/1996 | Conero et al. | 604/154 |
| 5,713,856 A | 2/1998 | Eggers et al. | 605/65 |
| 5,814,015 A | 9/1998 | Gargano et al. | |
| 5,836,910 A | 11/1998 | Duffy et al. | 604/65 |
| 5,941,846 A | 8/1999 | Duffy et al. | 604/65 |
| 6,428,509 B1 * | 8/2002 | Fielder | 604/154 |
| 6,652,489 B1 * | 11/2003 | Trocki et al. | 604/154 |

FOREIGN PATENT DOCUMENTS

| | | | |
|---|---|---|---|
| EP | 0 916 353 A | | 5/1999 |
| EP | 1 110 569 A2 | | 6/2001 |
| GB | 110569 | * | 6/2001 |

* cited by examiner

Primary Examiner—Nicholas D. Lucchesi
Assistant Examiner—Matthew F. DeSanto
(74) Attorney, Agent, or Firm—Fulwider Patton LLP

(57) ABSTRACT

A syringe plunger driver system capable of capturing syringes of widely varying sizes comprises a pair of asymmetric plunger retainer arms pivotally mounted to a plunger driver. The system includes a low profile driver having a length that exceeds its width so that it may be mounted adjacent control modules and other operational modules. The arms are biased toward each other and one arm is longer than the other with a notch on an inside edge to receive the tip of the shorter arm when capturing small syringe flanges. A rotation knob mounted to the front surface of the low profile driver forces the arms apart when rotated to a first rotation position. A force sensor is mounted in the driver to detect occlusions in the fluid line. A processor monitors the force sensed by the force sensor and provides an alarm if the force exceeds a threshold. The driver includes a force concentrator that defines a pushing surface adapted to press against a plunger flange so that the force applied to the plunger flange is concentrated at a defined location for more accurate measurement.

27 Claims, 10 Drawing Sheets

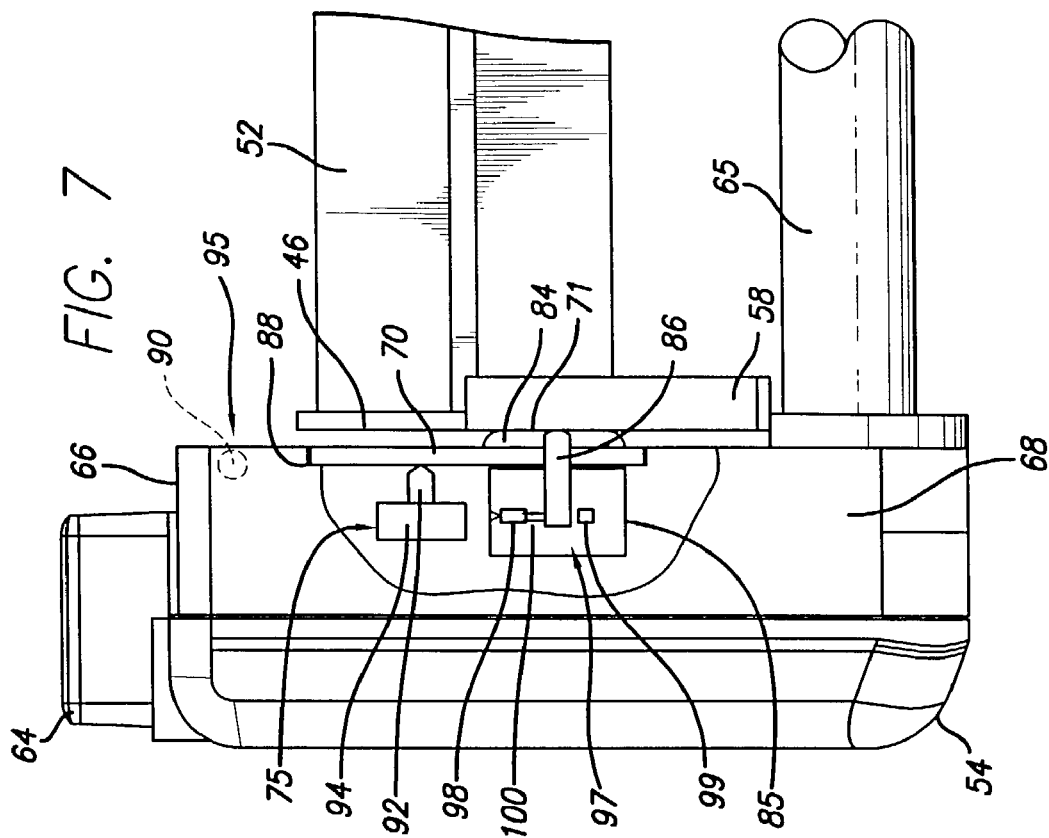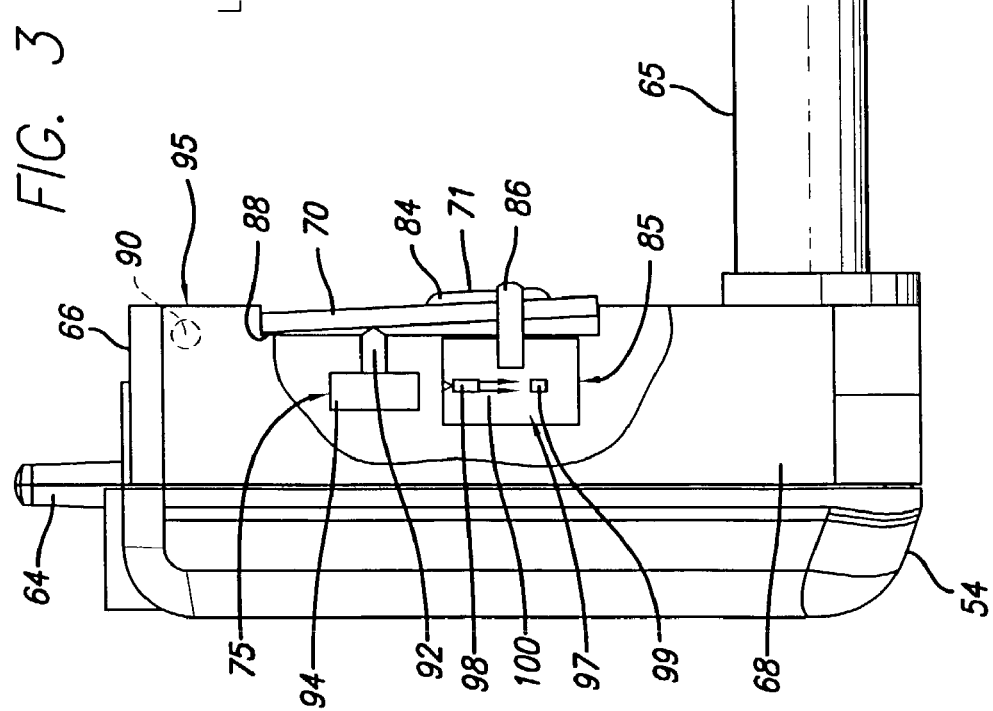

SYRINGE PLUNGER DRIVER SYSTEM

BACKGROUND

The invention is related generally to drive mechanisms for medical infusion pumps, and more particularly, to a system and method for driving the plunger of a syringe in a syringe pump.

The infusion of medical fluids, such as parenteral fluids, into the human body is accomplished in many cases by means of a syringe pump in which a syringe containing the parenteral fluid is mounted. Syringe pumps typically secure the syringe barrel in a fixed position and push or "drive" the syringe plunger into the barrel at a controlled rate to expel the parenteral fluid. A fluid administration set conducts the expelled parenteral fluid from the syringe barrel to the patient. Many syringe pumps have an elongated lead screw rotated by a motor and a screw drive mechanism such as a split nut that translates the rotational motion of the lead screw into linear motion. A syringe plunger driver is connected to the screw drive mechanism and to the syringe plunger for driving the plunger into the syringe barrel in accordance with the movement of the lead screw to expel the parenteral fluid.

Because syringes are of different sizes and are filled to different levels with infusion fluids, the extension of the plunger from the syringe barrel will differ from syringe to syringe. To accommodate such variations in the starting positions of the syringe plungers, screw drive mechanisms typically include a disengagement mechanism that the operator uses to disengage the screw drive mechanism from the lead screw threads. Once disengaged, the operator may move the plunger driver along the lead screw to the position of the extended syringe plunger, and then engage both the syringe plunger with the plunger driver and the threads of the lead screw with the screw drive mechanism at the new position. However, it is desirable that this disengagement mechanism and this plunger driver mechanism be easy to use and, preferably, be located at the same position so operation with one hand is possible.

Also, as is well known, syringes vary in size among manufacturers. Even syringes designed to contain the same quantity of fluid can vary substantially in outer dimensions of both length and diameter from manufacturer to manufacturer. In some prior pumps, only a very limited range of syringe sizes could be accommodated. They may be specified for use only with syringes of a particular manufacturer and only in a particular narrow size range. This limitation greatly restricts the usefulness of the pump. When a syringe from that manufacturer or one within the particular size range was not available, the pump could not be used and a different pump that would accommodate the syringe size had to be found, or the medical care facility would need to convince the supplier of the medical fluid to switch syringes or provide a new product line in which the desired syringes were used. Keeping health care costs as low as possible is desirable and requiring medical facilities to have different syringe pumps on hand that can accommodate different syringe sizes is less efficient and less cost effective than having a single syringe pump that can handle a wide range of syringe sizes.

Many plunger drivers include a plunger retainer having a pair of arms that engage the syringe plunger flange to retain it at the position of the plunger driver. These plunger retainer arms are biased inward towards each other to close around the flange and properly locate it in regard to a pushing surface that forms a part of the plunger driver. The pushing surface contacts the plunger flange and applies force to move the plunger into the syringe barrel to expel the syringe contents. Some plunger drivers include an anti-siphon feature on the plunger retainer, such as anti-siphon ledges on the plunger retainer arms, to prevent the plunger from moving into the barrel and emptying the syringe at a rate in excess of the programmed movement rate of the pushing surface when under a negative pressure condition downstream. It is desirable to avoid a siphoning condition as the rate of administration of a fluid from the syringe is typically prescribed for a patient and exceeding that rate may not meet the requirements of the prescription. This is particularly true in the case where the medicament is to be administered to the patient at a very low flow rate. Even a small amount of siphoning can exceed the prescribed rate.

Additionally, it has been found to be beneficial for the plunger driver, or some other device on the syringe pump, to verify that a syringe has been properly mounted in the syringe pump before the pump can be activated. If the syringe were not in the proper position and the plunger flange were to dislodge from the plunger driver during pump operation, some period of time may pass before an alarm is given, especially at low flow rates. It is also helpful for the plunger driver to be able to detect the existence of occlusions in the fluid line. Such detection can be performed by monitoring the force exerted against the plunger by the pushing surface of the plunger driver. In such systems, account should also be taken of the wide variations in shape of syringe plunger flanges with which the plunger driver engages. Many flanges are not flat but are instead rippled or otherwise deformed. Rather than being formed at a 90° angle to the plunger stem, many flanges are at other angles which may result in some difficulty unless the syringe pump has been designed to address such issues.

Performing all of the above functions for a wide range of syringe sizes and shapes would benefit medical care facilities in that only one pump would be needed. A syringe pump that is designed to handle syringes ranging from 1 cubic centimeter ("cc") to 60 cc regardless of the manufacturer and regardless of the shape of the syringe flange would be of value to medical care facilities in that this syringe range encompasses most of the syringes in common use today.

Hence, those skilled in the art have recognized a need for a syringe plunger driver system and method that are capable of handling syringes of widely varying sizes and shapes while still presenting a relatively easy system to use to the operator of the pump. Such a system and method should provide a mechanism to align, firmly engage, detect the presence of the plunger of each of the syringes specified for the pump and detect excess pressure in the fluid line. Further, such a system and method should be capable of resisting siphoning of the syringe contents from syringes of all sizes usable in the pump. The invention fulfills these needs and others.

SUMMARY OF THE INVENTION

The present invention is directed to a system and method for engaging syringe plungers of widely varying sizes with a single plunger driver, and more particularly for engaging syringe plungers associated with syringes ranging in size from 1 cc to 60 cc.

In a first aspect in accordance with the invention, a syringe plunger driver system is provided for engaging syringe plungers of different sizes, each plunger having a plunger piston, a plunger flange, and a plunger stem interconnecting the piston with the flange and each plunger forming a part of a syringe, each syringe having a barrel into and out of which the plunger moves, each plunger flange having an inner side facing the syringe barrel and an outer side, the syringe plunger driver system having a plunger driver adapted to move the syringe plunger into the syringe barrel in an operation mode, the syringe plunger driver system comprising a pushing surface located on the plunger driver adapted to press against the outer side of the plunger flange to move the flange toward the barrel during the operation mode, a plunger retainer located on the plunger driver adapted to capture the plunger of the syringe, the plunger retainer comprising a first arm mounted on the plunger driver and a second arm mounted on the plunger driver at a location spaced-apart from the first arm, said first and second arms being asymmetric, and a bias device connected with the first and second arms to bias the arms toward each other to capture the plunger flange between the first and second arms.

In a further aspect, the first and second arms have inside edges facing each other and the first arm comprises a notch on its inside edge for receiving a tip of the second arm. The arms are pivotally mounted to the plunger driver in selected locations such that the bias device will move the tip of the second arm into the notch of the first arm when no flange is present between the first and second arms. The first arm has a first length and the second arm has a second length, the second length being shorter than the first length, and the first and second arms are pivotally mounted to the plunger driver such that when a flange is properly positioned at the plunger driver in preparation for the operation mode, the arms will be equidistantly spaced from the flange on either side of the flange. The inside edge of each of the first and second arms comprises an anti-siphon ledge configured to engage the inner side of the plunger flange to restrain the plunger flange from movement toward the syringe barrel. In a more detailed aspect, the first and second arms are curved inwardly, whereby the first and second arms are adapted to capture syringe plunger flanges of different sizes.

In other aspects in accordance with the invention, the plunger driver has a rear surface that is mounted to a guide device that controls the movement of the plunger driver to be parallel with the plunger stem, the plunger driver having a front surface opposite the rear surface and defining a length of the plunger driver between the front and rear surfaces, and two lateral surfaces located between the front and rear surfaces, the lateral surfaces defining a width of the plunger driver, the length of the plunger driver being longer than the width. In a more detailed aspect, the driver system further comprises a control device mounted to the front surface of the plunger driver and interconnected with the first and second arms, the control device having a first position at which it moves the first and second arms outwardly into a syringe plunger non-engagement position in opposition to the bias device to permit easy loading of the syringe plunger flange to the plunger driver, and a second position at which the control device permits the first and second arms to capture the syringe plunger flange. Further, the control device comprises a rotation knob having a first rotation position at which it moves the first and second arms outwardly into the syringe plunger non-engagement position in opposition to the first bias device, and a second rotation position at which the rotation knob does not prevent the first and second arms from capturing the syringe plunger flange.

In other aspects, the bias device comprises a spring connected with the plunger retainer that biases the arms pivotally inward towards each other, the spring having enough force to retain a plunger flange in between the arms during the operation mode. The driver system further comprises a force detector located in the plunger driver and adapted to sense force exerted by the pushing surface against the plunger flange, the force detector outputting a force signal representative of the force exerted against the plunger flange. In more detailed aspects, the force detector is in contact with the pushing surface, the pushing surface comprises a movable flange contact plate, and the movable flange contact plate is pivotally mounted. Further, the driver system comprises a processor in communication with the force signal that compares the force signal against a threshold and provides an alarm signal if the force signal exceeds the threshold. In one embodiment, the syringe plunger driver system further comprises a force concentrator located on the plunger driver that defines the pushing surface, whereby force exerted against the plunger flange in operation mode is concentrated at the pushing surface of the force concentrator so that the force may be accurately detected.

In another aspect of the invention, a method is provided for capturing syringe plungers of different sizes at a plunger driver, each plunger having a plunger piston, a plunger flange, and a plunger stem interconnecting the piston with the flange, wherein each plunger forms a part of a syringe, each syringe having a barrel in which the plunger moves, each plunger flange having an inner side facing the syringe barrel and an outer side, the plunger driver adapted to move the syringe plunger into the syringe barrel in an operation mode, the method comprising the steps of opening first and second asymmetric arms mounted to the plunger driver away from each other far enough to permit easy loading of a syringe plunger to the plunger driver and, after a syringe plunger has been properly positioned in relation to the plunger driver, closing the first and second arms inward toward each other to capture the syringe plunger flange between the first and second arms. In a more detailed aspect, the step of closing the arms comprises the step of closing the first and second arms inward toward each other such that a tip of one of the arms moves into a notch on an inside edge of the other of the arms so that a syringe plunger flange of a relatively small size may be captured by the first and second arms. In another detailed aspect, the step of opening first and second asymmetric arms further comprises the step of rotating a rotation knob interconnected with the first and second arms to a first rotation position at which the rotation knob pivotally moves the first and second arms outward into a syringe plunger non-engagement position whereby easy loading of a syringe plunger in relation to the plunger driver is facilitated and, further, the step of closing the first and second arms inward toward each other comprises the steps of applying a biasing force to the first and second arms to bias them inward toward each other and moving the rotation knob to a second rotation position at which the rotation knob does not apply force opposing the biasing devices on the first and second arms so that the arms may move toward each other to capture a syringe plunger.

Other aspects and advantages of the invention will become apparent from the following detailed description and the accompanying drawings, illustrating by way of example the features of the invention.

BRIEF DESCRIPTION OF THE DRAWINGS

FIG. 3 is a partial cross-sectional side view of the plunger driver of FIG. 2 showing the force detector and plunger detector when the arms are in the syringe plunger non-engagement position shown in FIG. 2;

FIG. 7 is a partial cross-sectional side view of the plunger driver of FIG. 2 showing the force detector and plunger detector when the arms are in the closed position grasping a plunger flange in accordance with aspects of the present invention;

DETAILED DESCRIPTION OF PREFERRED EMBODIMENTS

Figure 1:
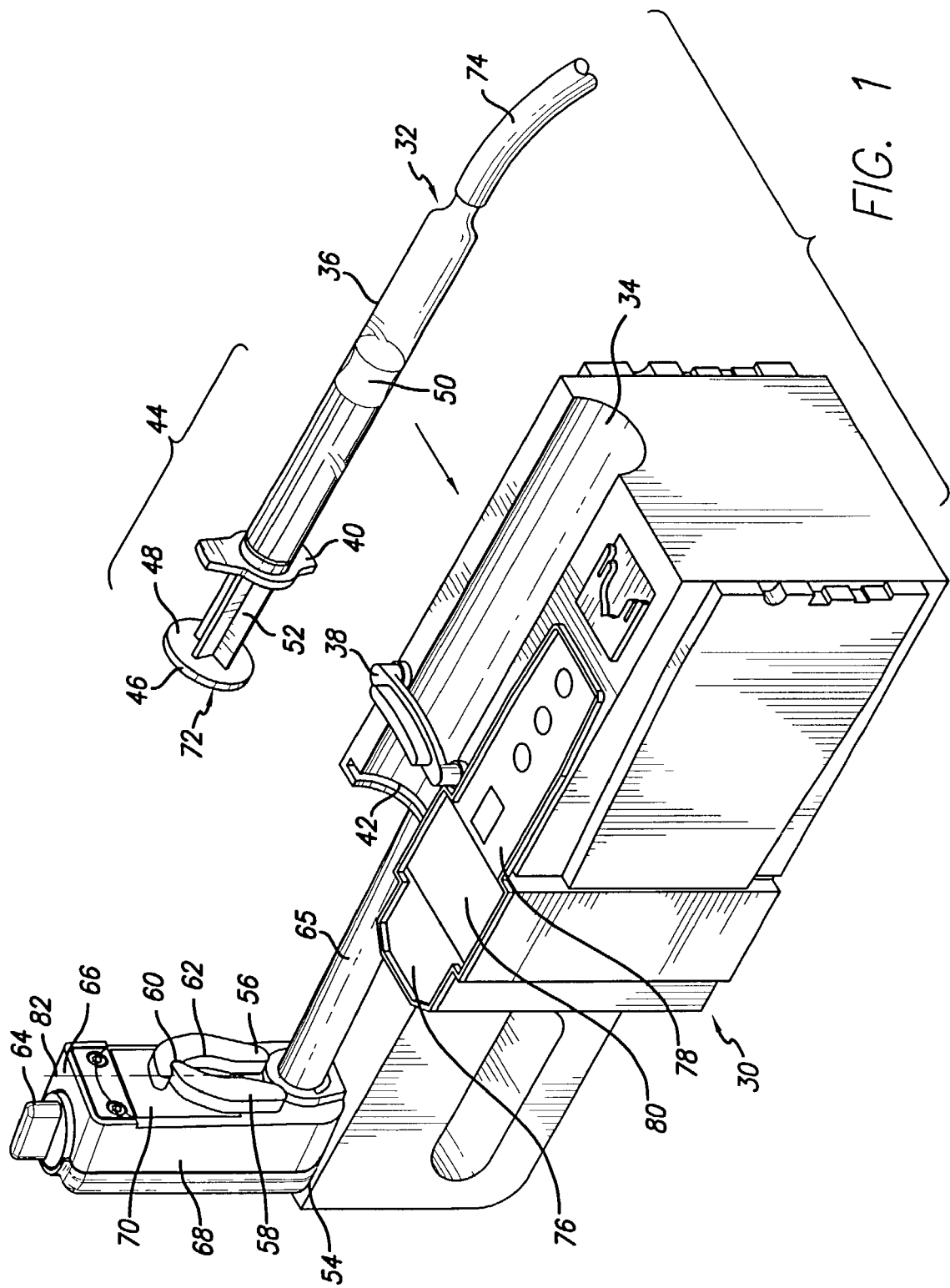
FIG. 1 is a perspective view of a syringe pump having a syringe plunger driver system in accordance with principles of the invention, and a typical syringe having a syringe barrel, a barrel flange, a syringe plunger, a syringe plunger stem, and a syringe plunger flange, with the barrel of the syringe connected to fluid administration set tubing which proceeds downstream to fluid communication with a patient (not shown), the arrow showing the location where the syringe barrel is mounted in the syringe pump.

Referring now to the drawings with more particularity, wherein like reference numerals designate like or corresponding elements among the several views, there is shown in FIG. 1 a perspective view of a syringe pump 30 having a syringe plunger driver system in accordance with the principles of the invention. A syringe 32 is shown next to the pump rather than mounted in the pump, for clarity of illustration, with an arrow indicating the mounting location. The syringe pump 30 includes a syringe cradle 34 in which the syringe barrel 36 will rest when properly mounted in the pump. The cradle 34 includes a syringe barrel clamp 38 to securely hold the syringe barrel 36 in a fixed position in the cradle 34 so that lateral movement is resisted. The syringe barrel clamp 38 is pivoted in this embodiment so that it may be moved into an open position to permit loading or removal of a syringe and a closed position in which it extends over the cradle 34 to hold a mounted syringe barrel 36. Furthermore, the syringe barrel flange 40 will be located in a barrel flange groove 42 in the pump 30 to immobilize the syringe barrel 36 from vertical movement during movement of the syringe, plunger 44 within the barrel 36.

The syringe plunger flange 46, having an inner side 48, is interconnected with a syringe piston 50 by a syringe plunger stem 52. When mounted in the syringe pump 30 properly, the plunger flange 46 is held by a plunger driver 54 with a plunger retainer comprising a pair of pivotally mounted, asymmetric arms, first arm 56 and second arm 58, shown in the closed position in FIG. 1. These plunger retainer arms 56 and 58 curve inwardly toward each other to grasp a plunger flange 46 mounted in the pump. The first arm 56 is longer than the second arm 58 such that, in the closed position, the tip of second arm 58 nests inside a notch 60 formed along the inside edge 62 of the first arm 56. A control device comprising a rotation knob 64 is used to disengage the plunger driver 54 from the threads of a lead screw (not shown) as well as control the positions of the first and second arms 56 and 58 to allow removal and insertion of a syringe plunger flange 46. Disengaging the plunger driver 54 from the threads of the lead screw permits the operator to move the driver 54 along the lead screw to the correct position to capture the plunger flange of a new syringe 32. As is well known, syringes may be provided for use with a syringe pump with different quantities of fluid and the plunger may be located at different positions in relation to the barrel. The ability to manually move the driver 54 permits the accommodation of syringes with different beginning plunger positions. A guide device 65 extends in one piece from the driver 54 to a point within the body of the pump 30. This extended length serves to prevent spilled or leaking fluids from reaching the lead screw.

Figure 11:
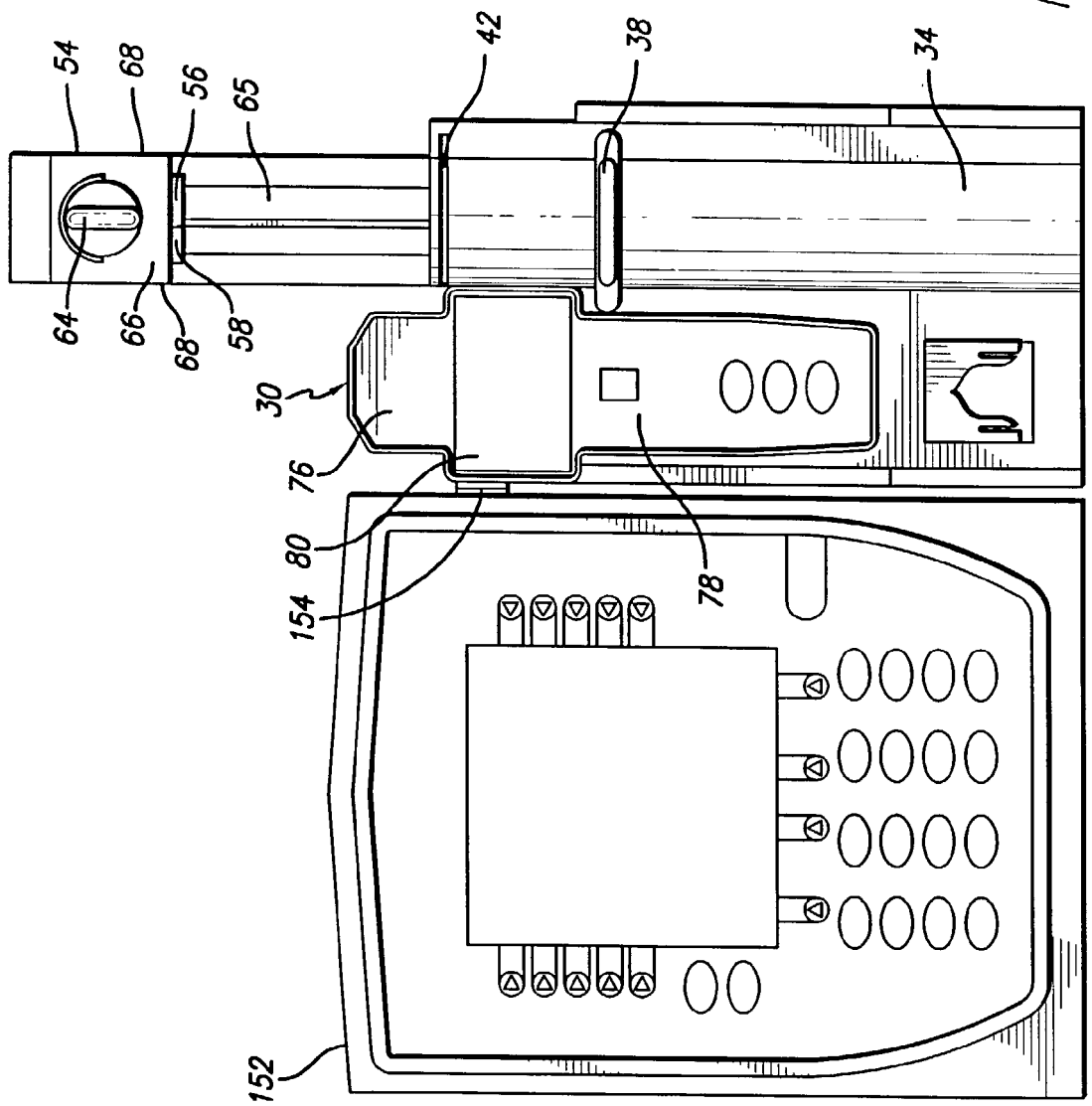
FIG. 11 shows a view of the syringe pump in accordance with aspects of the present invention mounted to a programming module that provides programming of the syringe pump as well as performing communications and other functions.
Figure 12:
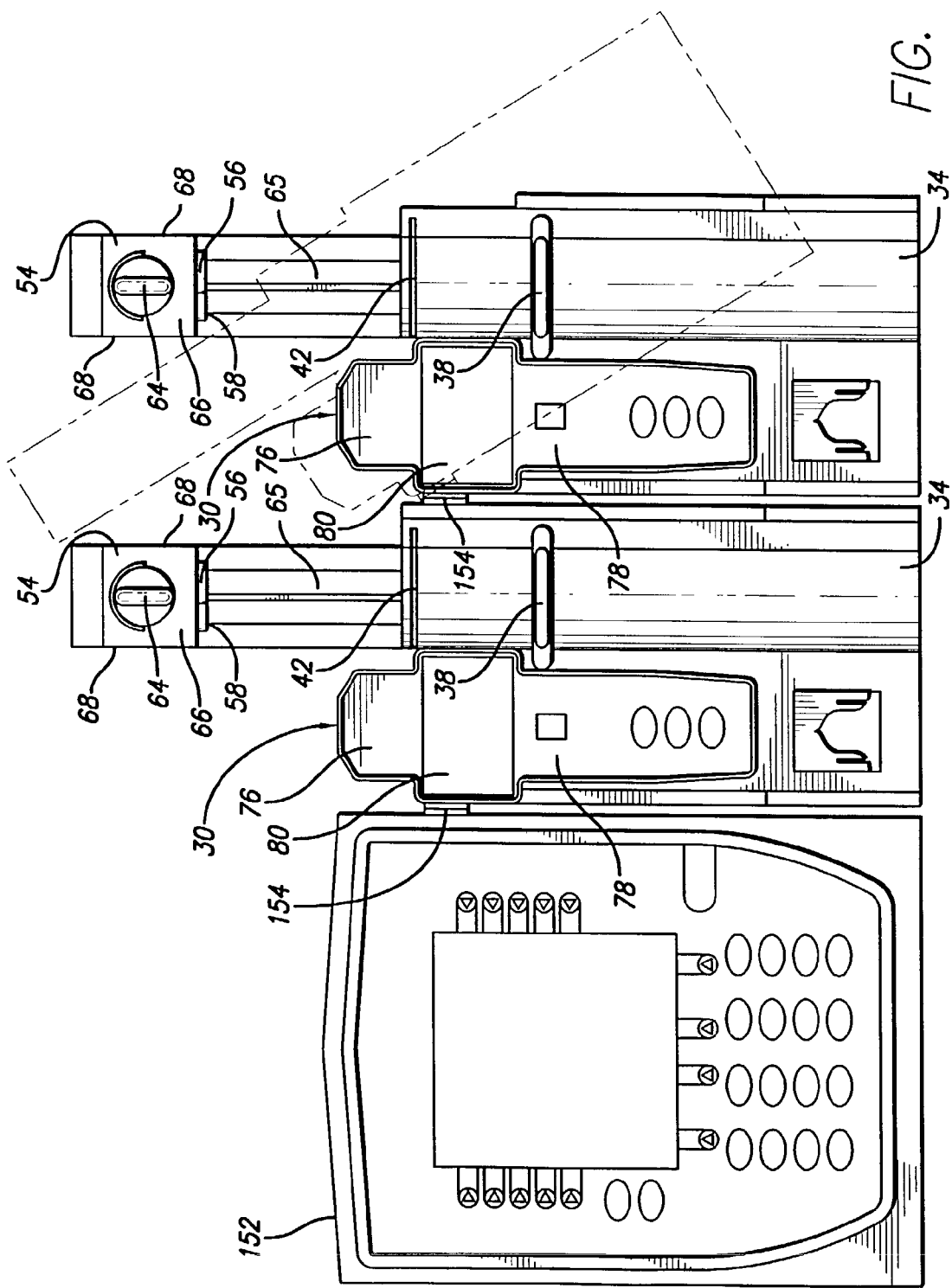
FIG. 12 shows the view of FIG. 11 but with a second syringe pump module mounted to the first, and shown in dashed lines is the angular movement required to remove the outer syringe pump module from the first.

The plunger driver 54 in this embodiment has a front surface 66 on which the rotation knob 64 is located, a rear surface (not shown) opposite the front surface 66, and two lateral surfaces 68. The length of the driver 54 between the front surface 66 and rear surface is longer than the width of the driver 54 between the lateral surfaces 68. This provides a narrow, low profile driver 54 that may be mounted adjacent control modules and other operational modules. As used herein, the terms "front" and "rear," as well as other terms such as "top," "bottom," "vertical" and "longitudinal," are consistent with the typical orientation of the syringe pump of the present invention, which is shown in FIGS. 11 and 12. However, these terms are merely used for reference. Then plunger driver 54 also includes a movable flange contact plate 70 that has a pushing surface 71 (shown in FIG. 2) that contacts the outer side 72 of the plunger flange 46 as the driver 54 moves forward toward the syringe barrel 36 pushing the plunger 44 into the barrel 36 of the syringe to expel the syringe contents through a fluid administration set tubing 74 to the patient when a syringe is mounted. The movable flange contact plate 70 is interconnected to a force detector 75 (shown in FIGS. 3 and 7) to detect occlusions in the fluid line. When the movable flange contact plate 70 exerts force against the plunger flange 46, a force sensor reports the detected force to a processor, that activates an alarm and optionally stops the operation of the pump if the force exceeds a threshold indicating an obstruction in the fluid pathway (see FIG. 8).

Also included with the pump 30 is a control panel 76 comprising multiple buttons 78 for control over the pump 30 as well as a display 80 used to present pump-specific information to the operator. The buttons 78 may allow the operator to program the pump 30 for the flow rate, the volume to be infused, and other pump parameters. The display 80 may present the programmed flow rate, the amount of fluid remaining to be infused, as well as alarms and other information.

A syringe inserted in the cradle 34 will align with the plunger driver 54 within a particular longitudinal range. The points where the lateral center lines of the syringes intersect the plunger driver will change according to the size of the syringe but only in one direction 82 along the driver 54.

Figure 2:
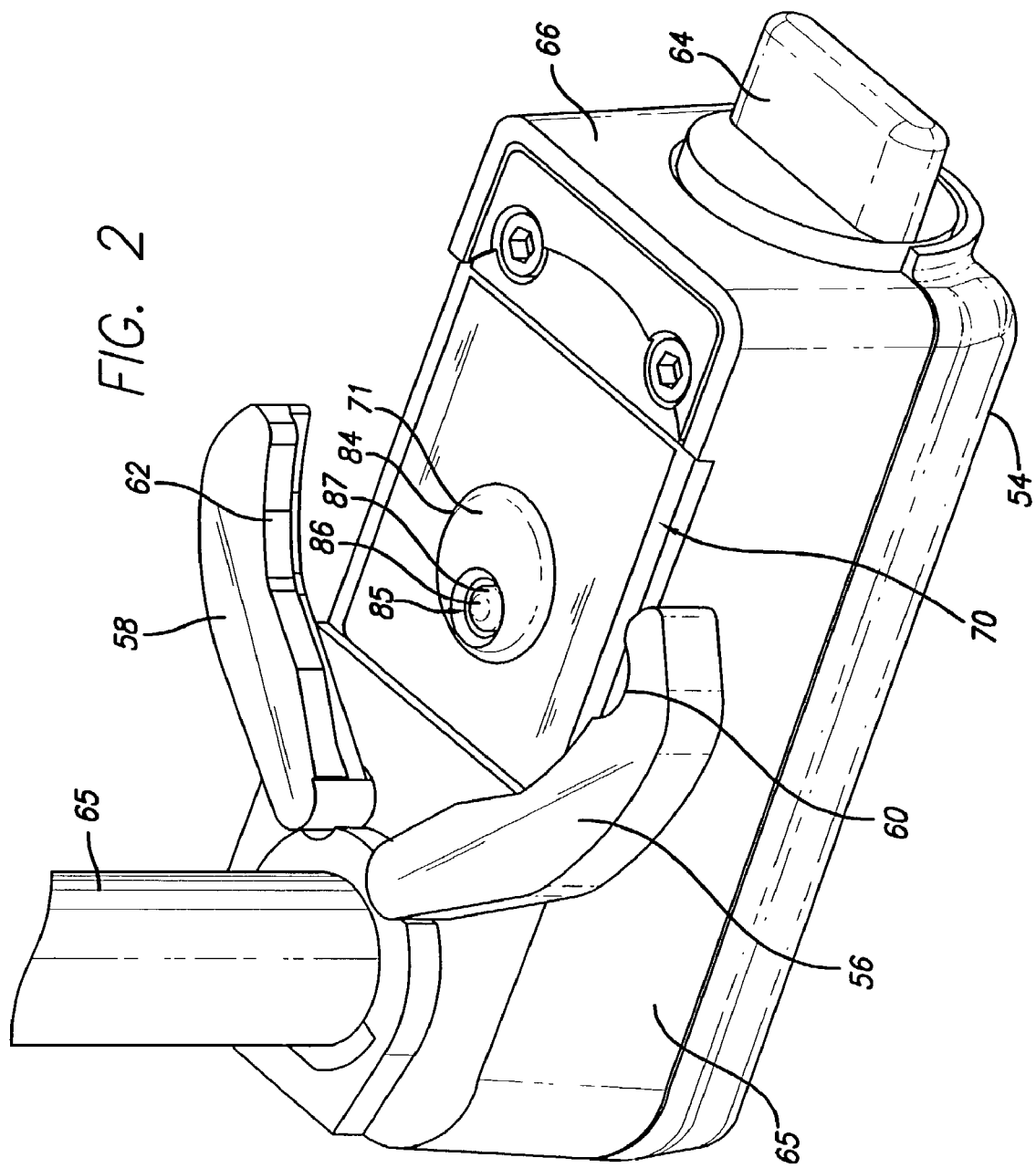
FIG. 2 is an enlarged perspective view of the plunger driver as shown in FIG. 1 with a rotation knob rotated to a first rotation position and first and second asymmetric plunger retainer arms consequently shown in a syringe plunger non-engagement position so that a movable flange contact plate, a force concentrator and a plunger detector can be seen.

Referring now to FIG. 2, the arms 56 and 58 are shown in the syringe plunger non-engagement position where the first and second arms 56 and 58 have been moved outward (pivoted away from each other). In this position, the driver 54 is ready to accept a syringe plunger. Shown in this view is the rotation knob 64 that has been moved to a first rotation position causing the first and second arms 56 and 58 to be in the syringe plunger non-engagement position. The rotation knob 64 also acts as a handle for the operator to hold when moving the driver 54 forward toward the syringe barrel 36 to the position of the plunger flange when a syringe is mounted. In one embodiment, the rotation knob 64 is interconnected to a rotation knob position detector 83 (shown in FIGS. 8 and 10) to indicate to a processor when the rotation knob is in its first rotation position so that operation of the pump motor may be disabled.

The movable flange contact plate 70 is also shown more clearly in FIG. 2. In this embodiment, the movable flange contact plate 70 has a force concentrator 84 protruding from its surface that defines the pushing surface 71. As is discussed in more detail below, the pushing surface 71 of the force concentrator 84 will contact the outer side 72 of the plunger flange 46 (see FIG. 1) as the driver 54 pushes against the plunger, thereby concentrating the force exerted by the movable flange contact plate 70 for more accurate measurement of the force.

Also included in this embodiment of a plunger driver 54 is a syringe plunger detector 85 having a detector button 86 used to detect the presence of a syringe. When the button 86 is depressed by a properly mounted syringe, the plunger detector 85 indicates to a pump processor (not shown) that a syringe is present thereby enabling operation of the pump. In one embodiment, the pump will not operate if the detector button 86 has not been depressed, as may happen with a mis-loaded syringe, or a syringe that has become dislodged, or in the case where a syringe has not been loaded whatsoever.

FIG. 3 presents a partially cut-away cross-sectional side view of FIG. 2 with the arms 56 and 58 removed, further showing the force detector 75 and the plunger detector 85. A recess 88 is formed in the plunger driver 54 to accommodate the movable flange contact plate 70. The movable flange contact plate 70 is attached to the plunger driver 54 inside recess 88 at a pivot point 90. The movable flange contact plate 70 is forced to protrude slightly outward in the vertical direction from the surface of the driver 54 toward a mounted syringe plunger flange due to a bias exerted against the flange contact plate 70 by an extension piece 92 that is coupled to a force sensor 94 located inside the driver 54. In FIG. 3, the position of the movable flange contact plate 70, protruding beyond the surface of the driver 54, is exaggerated to more clearly illustrate its operation. Likewise, the lengths of the detector button 86 and extension piece 92 are exaggerated for illustrative purposes. As the pushing surface 71 of the force concentrator 84 of the movable flange contact plate 70 exerts force against the plunger flange, the force sensor 94 detects the force through the extension piece 92 and transmits the sensed force to a processor for monitoring (described below in relation to FIG. 8). In one embodiment, the force sensor 94 and the extension piece 92 are integral with each other and are sold as a single unit. For instance, JP Technologies, 1430 Cooley Court, San Bernardino, Calif. 92508, manufactures a force sensor that has been found to work well. The force detector 75 in one embodiment has a small travel distance between the extremes of exerting no force against a syringe plunger to "bottoming out" the force sensor. For example, a travel distance of 0.076 cm (0.003 in.) was found to be preferable in one embodiment.

The plunger flange 46 of a properly loaded syringe contacts the movable flange contact plate 70 only at the pushing surface 71 of the force concentrator 84, thereby concentrating the force applied to the plunger flange by the driver 54 at a defined location. Plunger flanges sometimes have irregular outer sides 72 (FIG. 1). For example, the outer side 72 may have a rippled surface. Furthermore, the entire plunger flange may not even be perpendicular to the plunger stem 52 and instead may lie at an angle of other than 90° to the stem. Without the force concentrator 84, such irregularities could cause the plunger flange to contact the movable flange contact plate 70 at different locations along that plate 70 which could then cause the pushing force provided by the plate against the plunger flange to be located at different locations along the plate. Such different locations may be closer to or farther from the force detector 75 location. Because the plate 70 is pivotally attached at one end 95, applying the force of the plate to the syringe plunger at different distances from that end 95 may result in different force indications from the force detector 75. The force concentrator 84 serves to fix the contact area of the movable flange contact plate 70 regardless of the size of the plunger flange and regardless of any irregularities on or of the plunger flange. Hence, the force detector 75 can provide more accurate measurements of the force applied to the plunger, improving the ability to detect an occlusion in the fluid line.

In FIG. 3, the detector button 86 forming part of a plunger detector 85 is shown in the extended position. A spring 96 (shown in FIGS. 9 and 10) mounted internally to the driver 54 and in this embodiment consisting of a flat spring pressing against the detector button 86 is used to bias the detector button 86 outward (in the vertical direction towards a properly mounted syringe plunger flange). An optical sensor system 97 determines the presence and absence of a syringe plunger flange at the driver 54 by monitoring the position of the button 86. The optical sensor system 97 in this embodiment includes an optical beam transmitter 98 and an optical beam receiver 99. An optical beam 100 produced by the transmitter 98 is detected by the receiver 99 when the detector button 86 is in its forward position as shown in FIG. 3 indicating that no syringe has been mounted in the syringe pump. If however, no optical beam 100 is detected by the receiver 99, interruption of the beam by the detector button 86 is indicated and a detection signal is provided indicating the presence of a properly mounted syringe plunger flange. This situation will be shown and described in further detail in relation to FIG. 7, below.

For further details concerning a syringe plunger detector system similar to that shown and described here, and which would function acceptably in the detector system described here, see U.S. Pat. No. 5,545,140 to Conero, which is incorporated herein by this reference.

Another feature shown in FIGS. 2 and 3 is a bevel 87 formed about the tip of the button 86. This bevel 87 aids in syringe insertion into the pump 30 by allowing longitudinal motion during installation. The syringe plunger flange would strike the bevel 87 causing the button 86 to depress somewhat while the syringe is being loaded. Without the beveled surface formed on the button 86, the syringe would have to be loaded more in a horizontal manner into the driver 54. With the bevel 87, the syringe may be loaded either horizontally or longitudinally thus making operator use of the pump easier.

Figure 4:
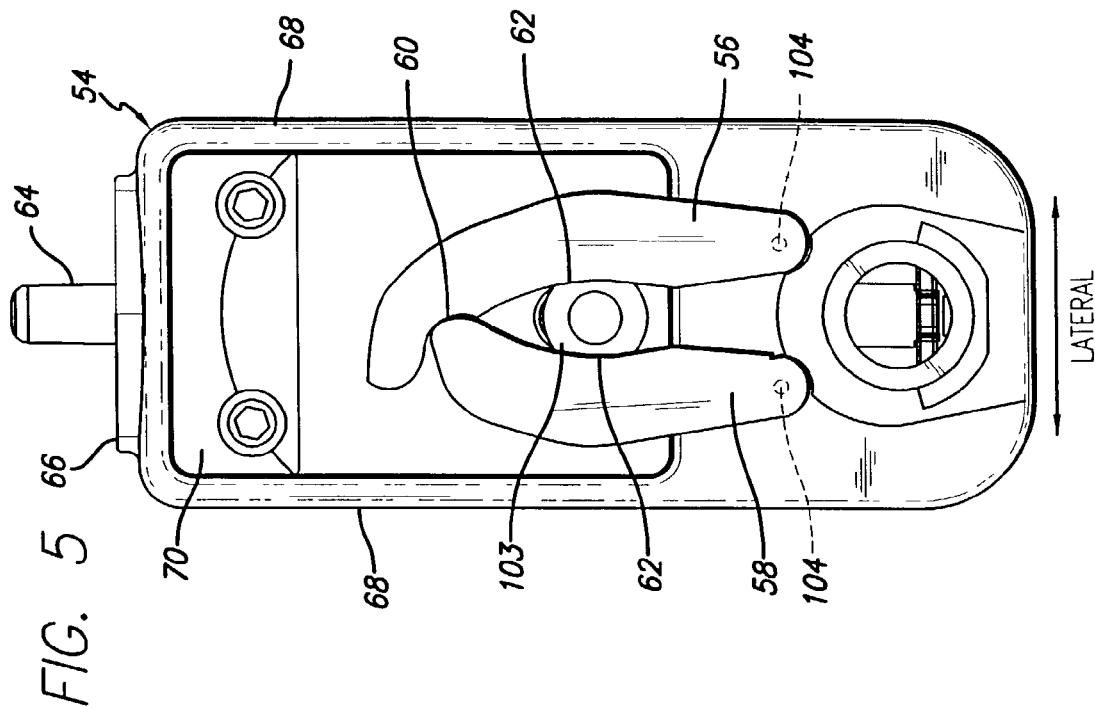
FIG. 4 is a view of the two asymmetric plunger retainer arms of the plunger driver shown in the previous figures grasping the plunger flange of a large 60 cc syringe in accordance with aspects of the invention, with the rotation knob shown rotated 90° from the position shown in FIG. 2 to a second rotation position.
Figure 5:
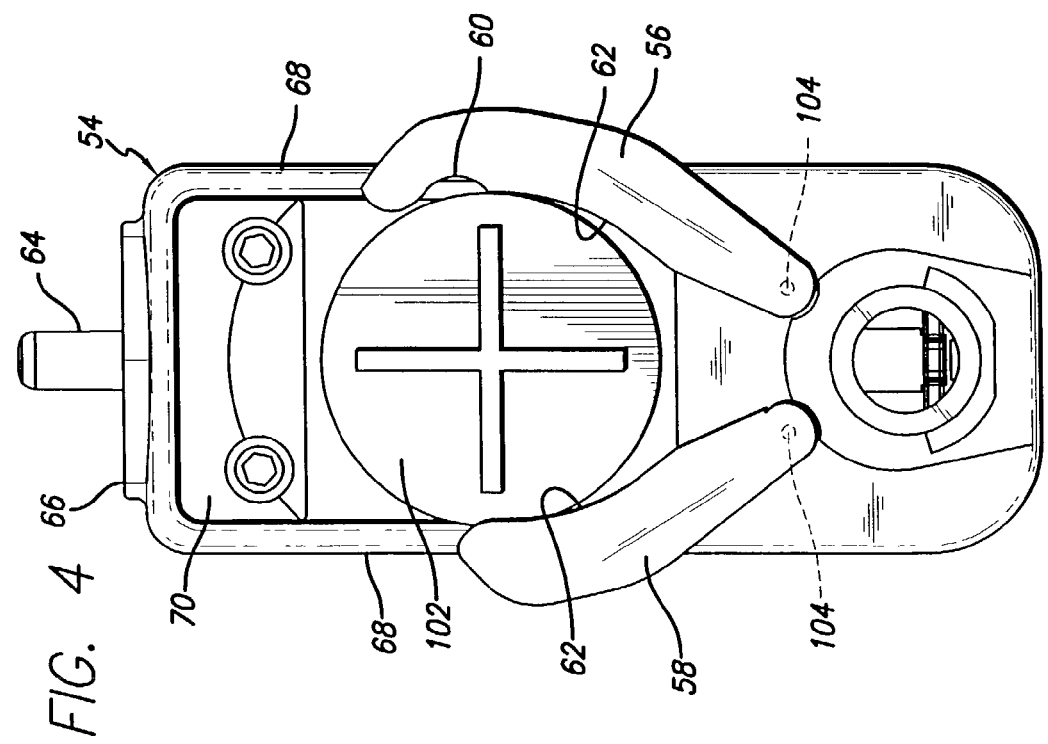
FIG. 5 is a view of the two asymmetric plunger retainer arms of FIG. 4 grasping a plunger flange of a small 1 cc syringe in accordance with aspects of the invention.
Figure 6:
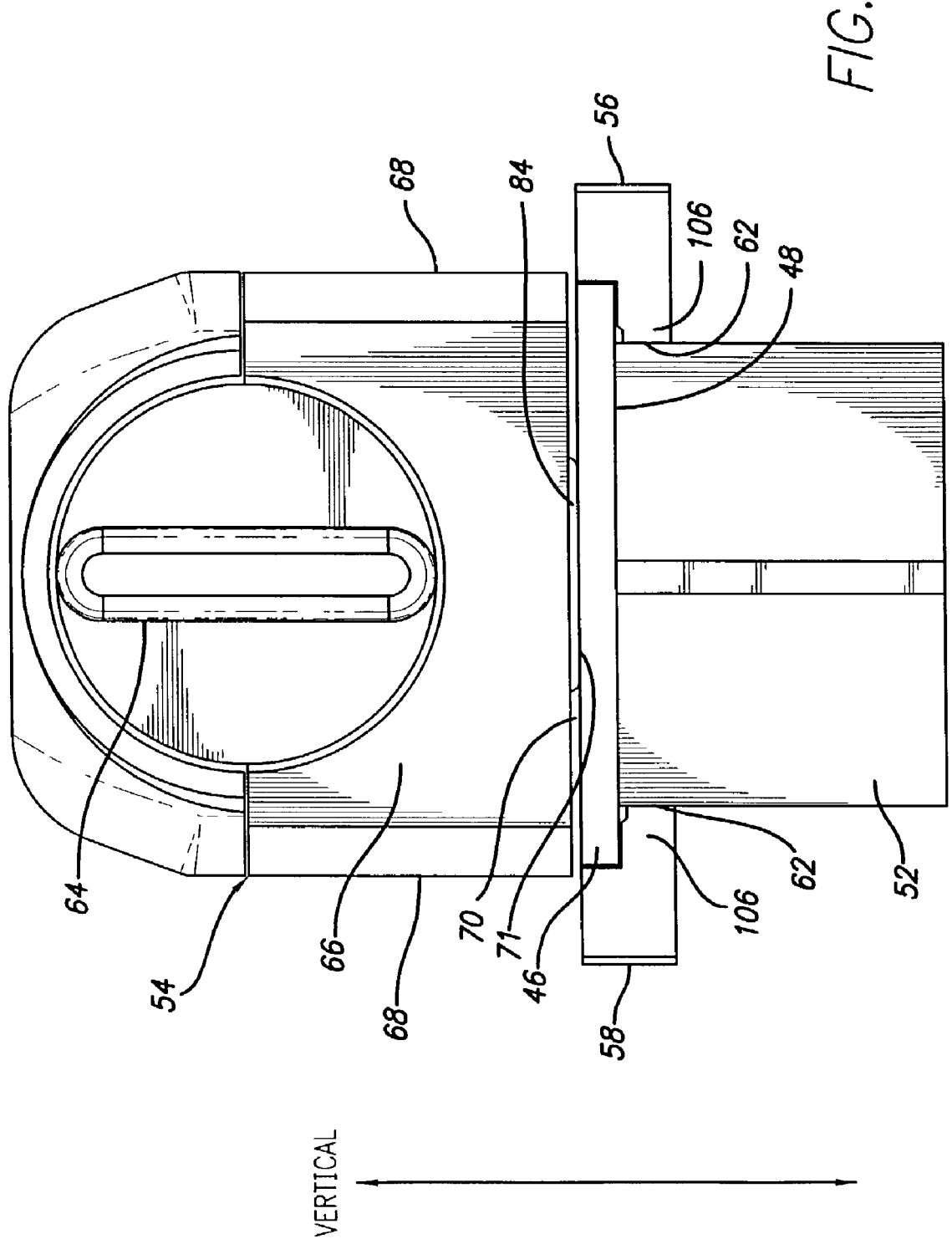
FIG. 6 is a front view showing the two asymmetric plunger retainer arms of FIG. 4 grasping the plunger flange in a radially inward direction with a clearer illustration of the interaction of the anti-siphon ledges of the arms controlling movement of the plunger flange in a vertical direction.

Turning now to FIGS. 4 through 7, the closed position of the first and second arms 56 and 58 is shown. In this configuration, the first and second arms 56 and 58 have pivoted inward toward each other to capture the plunger flange between themselves (FIGS. 4 and 5). The first and second arms 56 and 58 are spring loaded inward to provide a substantial clamping force against the plunger flange. To obtain this position, the rotation knob 64 has been moved to a second rotation position as shown in FIG. 6. As is shown in FIGS. 4 and 5, which present end views of the operation of the arms, the first and second arms 56 and 58 asymmetric and are self-adjusting to the size of plunger flange mounted in the pump. In FIG. 4, the first and second arms are engaging a large plunger flange 102 associated with a 60 cc syringe. In FIG. 5, the first and second arms 56 and 58 are engaging a small plunger flange 103 associated with a 1 cc syringe. The first and second arms 56 and 58 are located and pivoted about axes 104 such that the arms 56 and 58 are equidistant from the location at which a properly mounted syringe plunger flange 102 or 103 would be contacted by the driver 54 in the operation mode. As the arms 56 and 58 close inward to grasp the plunger flange 102 or 103, they tend to contact it in the lateral direction, thus aligning the plunger flange 102 or 103 with the driver 54.

In FIG. 5, the first and second arms 56 and 58 are shown engaging a 1 cc syringe plunger flange 103. It can be seen that when engaging the small plunger flange 103, the advantage of the asymmetric nature of the arms 56 and 58 is more apparent. The first arm 56 receives the second arm 58 such that the tip of the second arm 58 nests inside a notch 60 formed along the inside edge 62 of the first arm 56 and the small syringe plunger is thereby accommodated by the driver 54. This configuration may be compared to that shown in FIG. 4. In FIG. 4, the asymmetric arms 56 and 58 have captured a syringe plunger flange 102 of a large, 60 cc syringe. The plunger flange 102 is commensurately large; nevertheless, the arms 56 and 58 have effectively captured it and properly located it laterally (centered) in relation to the driver 54. Thus the unique configuration of the asymmetric arms 56 and 58 enables the driver 54 to capture a very small syringe as well as a very large syringe. In most cases, medical facilities will have no need for syringes outside this range of sizes and therefore, only one syringe pump will be needed for all infusions from syringes.

Referring now to FIG. 6, a front view of the engagement of the first and second arms 56 and 58 with the plunger flange 46 is shown. The first and second arms 56 and 58 further include anti-siphon ledges 106 located on their inside edges 62 that contact the inner side 48 of the plunger flange 46 to resist siphoning. When mounted in the syringe pump, the plunger flange 46 is located between the anti-siphon ledges 106 of the first and second arms 56 and 58 and the movable flange contact plate 70 located on the driver 54. The first and second arms 56 and 58 contact the flange 46 in a lateral direction. If the syringe should be subject to a siphoning action that would tend to pull the plunger into the syringe at a faster rate than programmed in the pump 30, the anti-siphon ledges 106 of the first and second arms 56 and 58 will restrain the plunger flange 46 from such movement and prevent emptying of the syringe in an uncontrolled manner. When operating in the normal mode, the driver 54 will move forward until the movable flange contact plate 70 contacts the plunger and will then push the plunger into the syringe to expel the contents of the syringe at the programmed rate. The barrel of the syringe is held stationary by disposing the barrel flange 40 in the flange groove 42 as shown in FIG. 1 and the plunger can then move relative to the barrel.

FIG. 7 shows the position of the movable flange contact plate 70 and detector button 86 when a syringe is loaded. Force exerted by the pushing surface 71 of the force concentrator 84 of the movable contact plate 70 when driving a plunger causes the extension piece 92 to communicate the driving force to the force sensor 94. In the case of an obstruction in the fluid pathway 74 (FIG. 1), the force exerted on the force concentrator 84 will increase and will be sensed by the force sensor 94. The force detector is indicated collectively by numeral 75 and includes the force sensor 94 and the extension piece 92.

Figure 8:
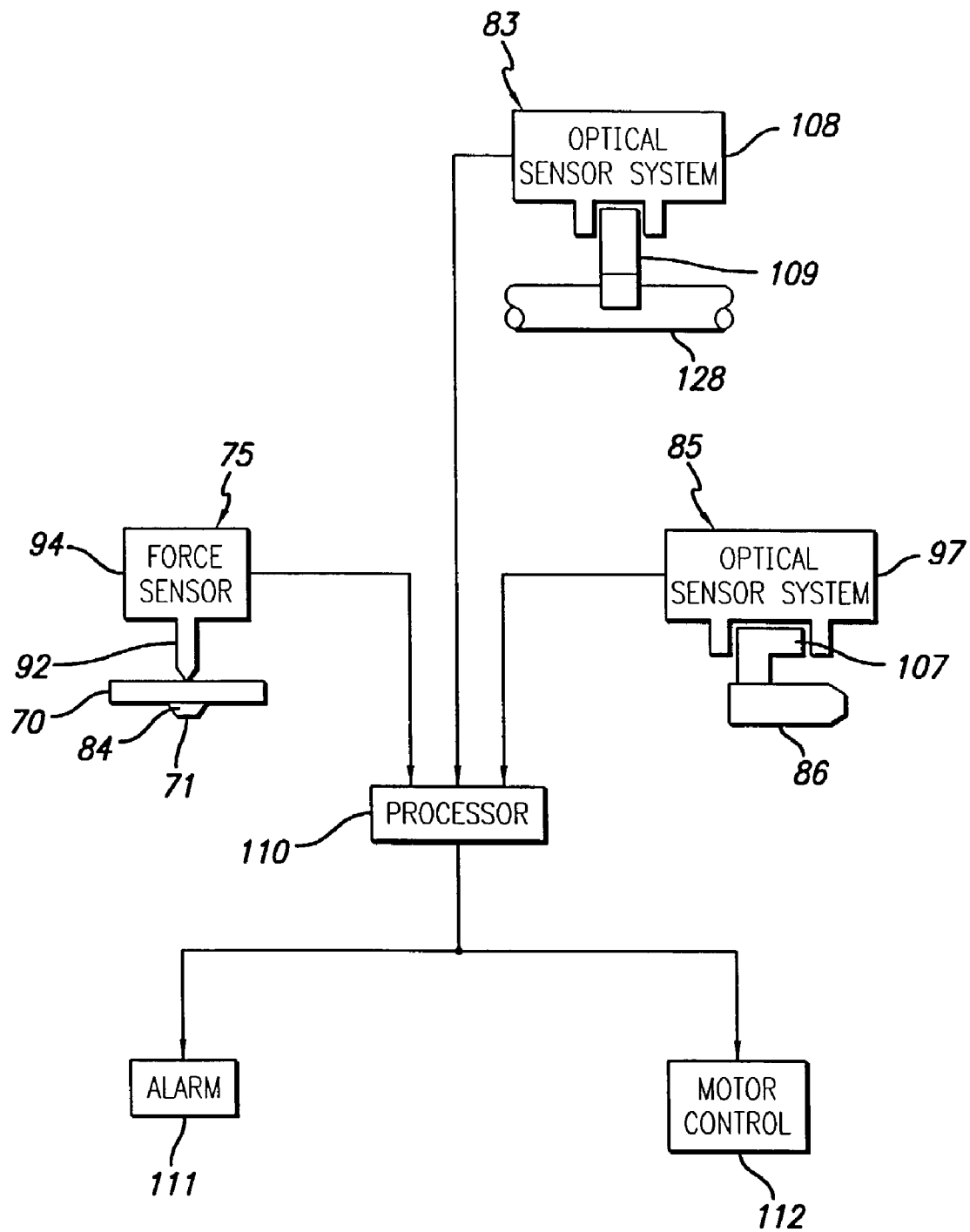
FIG. 8 is a block diagram showing a processor interconnected with the force detector and the plunger detector shown in previous figures, and processing the force detector signal and the plunger detector signal to determine if alarms should be provided as well as providing motor control.
Figure 9:
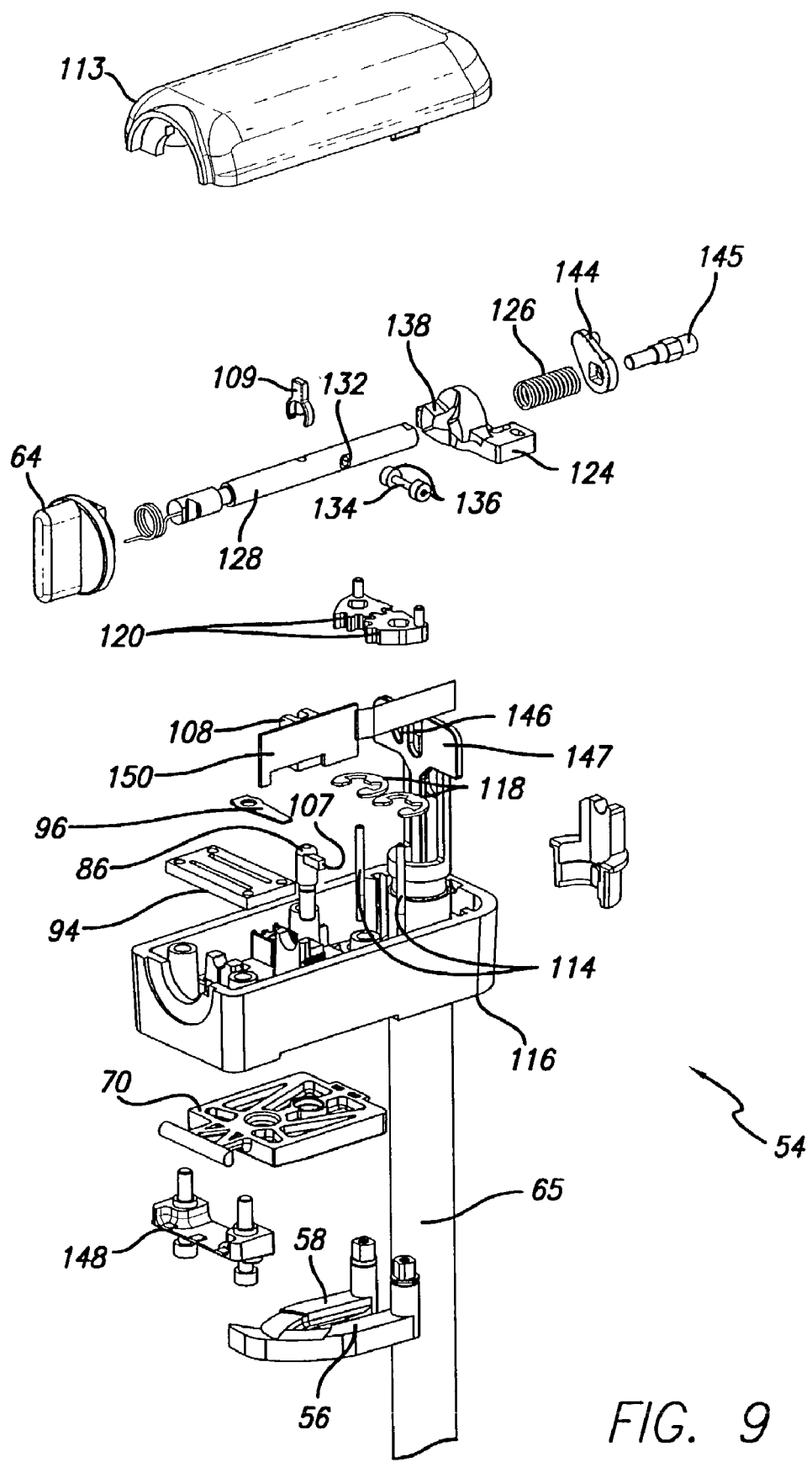
FIG. 9 is an exploded view of an embodiment of a plunger driver incorporating principles of the invention, showing the asymmetric plunger retainer arms, the rotation knob and the biasing means of those arms.
Figure 10:
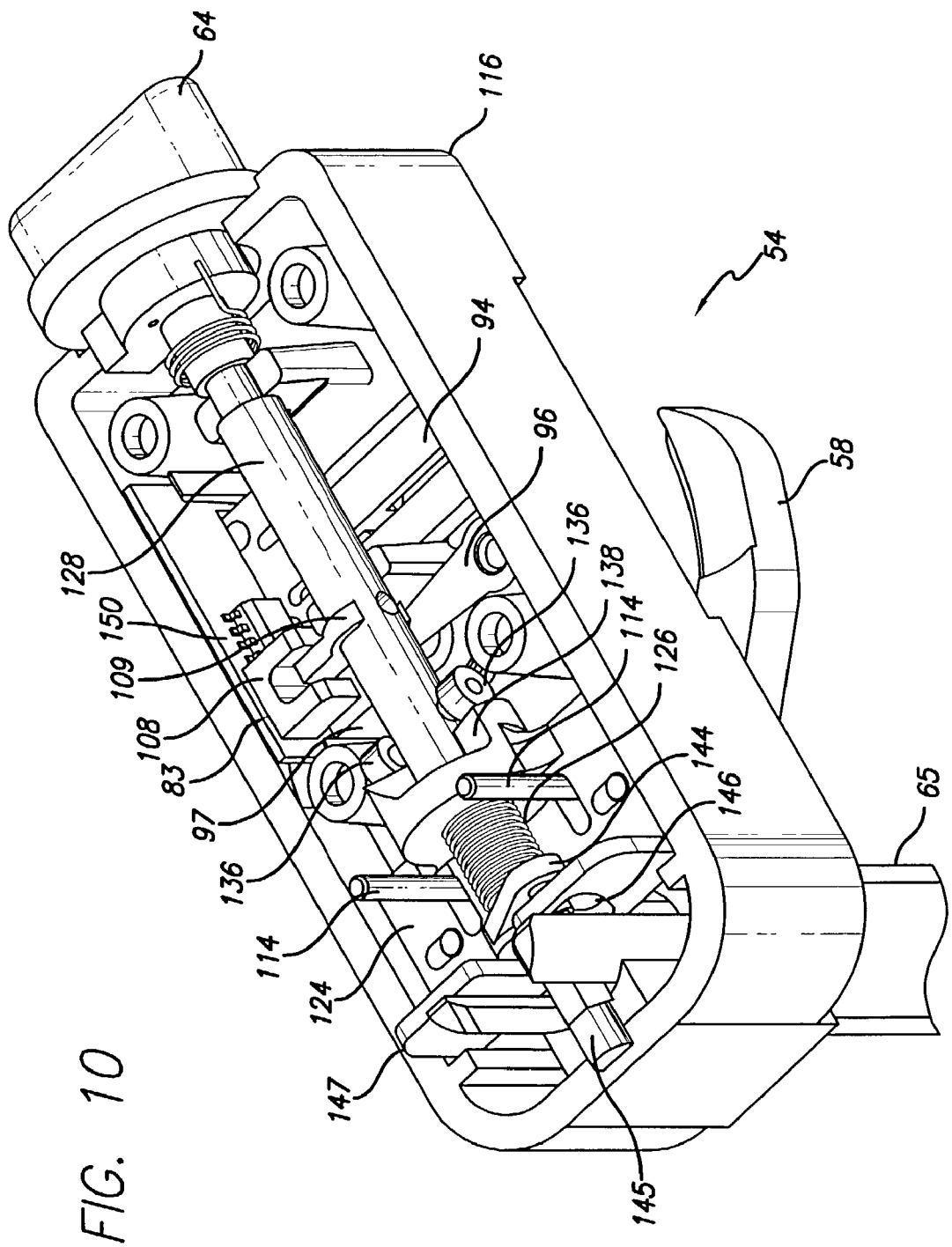
FIG. 10 shows a perspective assembled view of the plunger driver shown in FIG. 9 with the top housing removed and certain components visible from the top of the plunger driver.

Also shown in FIG. 7 is the detector button 86 that has been depressed by the mounted syringe. When the detector button 86 is depressed, it breaks the optical beam 100 provided by the optical transmitter 98. The output of the optical receiver 99 therefore changes and that change may be used to indicate the presence of a syringe mounted in the pump. For reference, FIG. 7 also indicates the direction referred to as "longitudinal" herein. In words, the longitudinal direction is the direction one would follow to mount a syringe barrel into the cradle of the syringe pump (see FIG. 1). In FIG. 8, an optical sensor system 97 that includes a flag 107 coupled to the detector button 86 is shown. In this embodiment, the flag 107 breaks the optical beam 100 when the button 86 is depressed. An embodiment with a flag 107 is also shown in FIG. 9. In one embodiment, the rotation knob position detector 83 includes an optical sensor system 108, similar to the optical sensor system 97 described with respect to the plunger detector 85, which also uses a flag 109 (see FIGS. 8 and 10). As shown in FIG. 10, when the rotation knob is rotated to a first position, the flag 109 interrupts a beam from the optical sensor system 108, indicating that the arms have opened in the syringe plunger nonengagement position. Such flags for use in optical sensor systems are well known and no further discussion is provided here.

The syringe pump 30 includes a processor 110 as shown in FIG. 8 that controls various aspects of operation. As further shown in FIG. 8, the processor 110 is connected either directly or indirectly to the force sensor 94 and to the optical sensor systems 97 and 108. Based on the signals received from these devices, and other signals, the processor 110 controls the movement of the driver 54. For example, if the processor 110 does not receive the correct signal from the optical sensor system 108 indicating that the rotation device is in the second rotation position (arms closed) and/or the optical sensor system 97 indicating that a syringe plunger has been detected, the processor 110 will provide a control signal to the motor control 112 that will prevent motor movement. In such case, the driver 54 cannot be moved by the motor. Similarly, if the pump had been in operation and the signal indicates that the plunger is not present, as would occur if the syringe became dislodged, the processor 110 would issue an alarm 111 as well as provide a signal to the motor control 112 to stop movement of the motor.

Force sensor 94 detects force from the extension piece 92 and outputs a force signal to a processor 110, shown in FIG. 8, which activates an alarm 111 when the force exceeds a threshold. In addition, as shown in FIG. 8, the processor 110 may provide a signal to the motor control 112 to stop the motor.

Referring now to FIG. 9, an exploded view of the parts of the driver 54 is presented. Additionally, FIG. 10 shows the assembly of the parts of the driver 54 shown in FIG. 9 except that the top housing 113 has not been installed so that the internal mounting of the various parts may be seen. As already described, there are first and second arms 56 and 58 used to grasp the plunger flange 46 of the inserted syringe (not shown). The first and second arms 56 and 58 are individually pivoted and are spring biased to close toward each other. Each arm 56 and 58 is connected to an anchor pin 114 extending inside the housing and is secured by a "C" clip 118. The arms 56 and 58 are coupled to inner crank arms 120 that are connected to a slider plate 124. Movement of the slider plate 124 causes the inner crank arms 120 to rotate and, consequently, the arms 56 and 58 to pivotally open and close about their axes 104 (FIGS. 4 and 5). The slider plate 124 is spring biased 126 in the direction that tends to cause the arms 56 and 58 to move toward each other into the closed position (FIG. 1).

The rotation knob 64 is interconnected to the slider plate 124 to control its movement and to thereby control the position of the arms 56 and 58. When the knob 64 is rotated in a predetermined direction, it will cause the arms to open in opposition to the spring bias 124 to thereby permit loading of a syringe. The rotation knob 64, positioned on the front of the driver 54, is coupled to a shaft 128 extending inside the driver 54. The shaft 128 has a hole 132 extending perpendicular to the longitudinal axis of the shaft 128. A bearing shaft 134 is inserted through the hole 132 and has two bearings 136 on either end of it.

When the rotation knob 64 is rotated to its first rotation position, the shaft 128 and the bearing shaft 134 are likewise rotated. The bearings 136 are located adjacent a ramp portion 138 of the slider plate 124 and engage it as they are rotated. The ramp portion 138 is configured so that, as the bearing shaft 134 and the bearings 136 are rotated along with the rotation knob 64 to its first position, the bearings 136 exert force against the ramp portion 138 causing the slider plate 124 to move longitudinally compressing spring 126. This movement of the slider plate 124 causes the arms 56 and 58 to move to the syringe plunger non-engagement position shown in FIG. 2.

When the rotation knob is turned to its second rotation position, the spring 126 tends to return to its uncompressed position, moving the slider plate 124 back towards the rotation knob 64. This causes the arms 56 and 58 to move to the closed position via the inner crank arms 120. If a syringe is loaded in the pump, the arms 56 and 58 will capture the plunger flange as they close inward towards each other, thus accommodating various sized plunger flanges. Because a single slider plate 124 and single biasing spring 126 interconnect both arms, the arms will tend to move the same amount toward each other at the same time and thereby center any syringe flange that is located between them.

The rotation knob is also interconnected with the screw drive mechanism (not shown) to allow engagement and disengagement with the lead screw. As the rotation knob is turned to its first rotation position, the shaft 128 drives a cam 144, locked into position on the shaft 128 by a shaft extension piece 145, that operates to declutch the split nut at the lead screw (neither is shown). A cam pin (not shown) captured in an opening 146 in a split nut control rod 147 forces the split nut control rod 147 to move downward as the cam 144 is driven. This action releases the split nut from a lead screw, and the plunger driver may be moved along the lead screw to the position of the extended syringe plunger. When the rotation knob is turned to its second rotation position, the rod 147 is forced upwards and the screw drive mechanism is again engaged with the threads of the lead screw at the new position. A spring bias mechanism (not shown) operates to bias the split nut closed and into engagement with the lead screw. Such mechanisms are well known and no further details are provided here.

FIGS. 9 and 10 also show further details of the force detector 75 and the plunger detector 85. The movable flange contact plate 70 is connected to the bottom housing 116 with an attachment piece 148. The attachment piece 148 allows the movable flange contact plate 70 a small degree of movement so that it will depress slightly about its pivot point 90 (FIG. 7) when pressed by a mounted syringe and exert force against the extension piece 92 of the force sensor 94. The force sensor 94 is also connected to a circuit board 150 which receives signals from the force sensor 94. The circuit board 150 also receives signals from the optical sensor systems 97 and 108.

In operation, the rotation knob 64 is rotated from its bias position (FIG. 1) to a first rotation position (FIG. 2), pivotally moving the first and second arms 56 and 58 outward (FIG. 2) for easy loading of a syringe plunger to the driver 54. In this position, the screw drive mechanism (not shown) is disengaged so that the driver 54 may be moved to the correct position to capture the plunger flange. Once the driver 54 is properly positioned, the rotation knob 64 is turned to a second rotation position, its bias position, engaging the screw drive mechanism and closing the first and second arms 56 and 58 inward toward each other to capture the plunger flange 102 or 103 (FIGS. 4 and 5). When capturing a small syringe, the first and second arms 56 and 58 close such that the tip of the second arm 58 moves into a notch 60 on the inside edge 62 of the first arm 56 as shown in FIG. 5. With the first and second arms 56 and 58 securely grasping the plunger flange 102 or 103, operation of the pump 30 may then begin.

FIG. 11 presents a perspective view of the syringe pump 30 mounted to a programming module 152, together forming a modular patient care system. Systems of this sort are described in U.S. Pat. No. 5,713,856 entitled "Modular Patient Care System" to Eggers et al., U.S. Pat. No. 5,941,846 entitled "Method and Apparatus for Power Connection in a Modular Patient Care System" to Duffy et al., and U.S. Pat. No. 5,836,910 entitled "Method and Apparatus for Logical Addressing in a Modular Patient Care System" to Duffy et al., which are incorporated herein by this reference. The programming module 152 in FIG. 11 performs various functions for the pump such as programming and communications. In addition to the syringe pump 30 that is mounted to the programming module 152, other modules, such as those providing patient monitoring or therapies, may also form part of the patient care system. The programming module 152 provides a centralized interface for the various attached modules. In one embodiment of the present invention, the driver 54, as described previously, provides a low profile so that it may be mounted adjacent other modules.

Because of its low profile, it may be tilted toward the programming module 152 in this case to remove it from the mechanical and electrical connections that are located at approximately numeral 154 in FIG. 11. The advantage of such a low profile can be seen more dramatically when two syringe pump modules 30 are mounted to each other and when one must be removed, as shown in dashed lines in FIG. 12.

From the foregoing, it will be appreciated that the plunger driver system in accordance with the principles of the invention provides a versatile system to accept a wide size range of syringes.

Although specific embodiments of the invention have been described and illustrated it is clear that the invention is susceptible to numerous modifications and embodiments within the ability of those skilled in the art, and without the exercise of the inventive faculty. Thus, it should be understood that various changes in form, detail and application of the present invention may be made without departing from the spirit and scope of the invention.

What is claimed is:

1. A syringe plunger driver system for engaging syringe plungers of different sizes, each plunger having a plunger piston, a plunger flange having an outer diameter, and a plunger stem interconnecting the piston with the flange, and each plunger forming a part of a syringe, each syringe having a barrel in which the plunger moves, each plunger flange having an inner side facing the syringe barrel and an outer side, the syringe plunger driver system having a plunger driver adapted to move the syringe plunger into the syringe barrel in an operation mode, the syringe plunger driver system comprising:

a pushing surface located on the plunger driver adapted to press against the outer side of the plunger flange to move the flange toward the barrel during the operation mode wherein the pushing surface has a size that is large enough to engage plunger flanges ranging from relatively small to relatively large outer diameters;

a plunger retainer located on the plunger driver adapted to capture adjacent the pushing surface of the plunger driver syringe plunger flanges ranging from relatively small to relatively large outer diameters, the plunger retainer comprising:

a first arm having a first length and an inner edge, the first arm being movably mounted on the plunger driver to engage a plunger flange at a first location thereof;

a second arm movably mounted on the plunger driver having a second length shorter than the first length of the first arm to engage a plunger flange at a different location than the first arm such that the first and second arms apply force towards each other to the plunger flange to capture the flange;

wherein the ranges of movement of the first and second arms are selected so that the first and second arms engage plunger flanges ranging from relatively small to relatively large outer diameters and in the operation mode, the plunger retainer having a plurality of operating configurations at least one of which comprises a tip of the second arm contacting the inner edge of the first arm when engaging a plunger flange that is relatively small and a second of which comprises the first and second arms not touching each other when engaging a plunger flange that is relatively large; and a bias device connected with the first and second arms to bias the arms toward each other to capture the plunger flange between the first and second arms.

2. The syringe plunger driver system of claim 1 further comprising a force detector located in the plunger driver and adapted to sense force exerted by the pushing surface against the plunger flange, the force detector outputting a force signal representative of the force exerted against the plunger flange.

3. The syringe plunger driver system of claim 2 wherein the force detector is in contact with the pushing surface.

4. The syringe plunger driver system of claim 3 wherein the pushing surface comprises a movable flange contact plate.

5. The syringe plunger driver system of claim 4 wherein the movable flange contact plate is pivotally mounted.

6. The syringe plunger driver system of claim 2 further comprising a processor in communication with the force signal that compares the force signal against a threshold and provides an alarm signal if the force signal exceeds the threshold.

7. The syringe plunger driver system of claim 2 wherein the plunger driver includes a force concentrator that defines the pushing surface, whereby the force exerted against the plunger flange is concentrated on the pushing surface of the force concentrator so that the force detector can accurately sense the force exerted.

8. The syringe plunger driver system of claim 1 wherein the first and second arms have inside edges facing each other and the first arm comprises a notch on its inside edge for receiving the tip of the second arm.

9. The syringe plunger driver system of claim 8 wherein the arms are pivotally mounted to the plunger driver in selected locations such that the bias device will move the tip of the second arm into the notch of the first arm when no flange is present between the first and second arms.

10. The syringe plunger driver system of claim 9 wherein the first and second arms are pivotally mounted to the plunger driver such that when a flange is properly positioned at the plunger driver in preparation for the operation mode the arms will be equidistantly spaced from the flange on either side of the flange.

11. The syringe plunger driver system of claim 8 wherein the inside edge of at least one of the first and second arms comprises an anti-siphon ledge configured to engage the inner side of the plunger flange to restrain the plunger flange from movement toward the syringe barrel.

12. The syringe plunger driver system of claim 1 wherein the plunger driver has a rear surface that is mounted to a guide device that controls the movement of the plunger driver to be parallel with the plunger stem, the plunger driver having a front surface opposite the rear surface and defining a length of the plunger driver between the front and rear surfaces, and two lateral surfaces located between the front and rear surfaces, the lateral surfaces defining a width of the plunger driver, the length of the plunger driver being longer than the width.

13. The syringe plunger driver system of claim 12 further comprising a control device mounted to the front surface of the plunger driver and interconnected with the first and second arms, the control device having a first position at which it moves the first and second arms outwardly into a syringe plunger non-engagement position in opposition to the bias device to permit easy loading of the syringe plunger flange to the plunger driver, and a second position at which the control device permits the first and second arms to capture the syringe plunger flange.

14. The syringe plunger driver system of claim 13 wherein the control device comprises a rotation knob having a first rotation position at which it moves the first and second arms outwardly into the syringe plunger non-engagement position in opposition to the first bias device, and a second rotation position at which the rotation knob does not prevent the first and second arms from capturing the syringe plunger flange.

15. The syringe plunger driver system of claim 1 wherein the first and second arms are pivotally mounted to the plunger driver at positions that are equidistant from a location where a syringe plunger flange would be properly mounted to the plunger driver in the operation mode, the first and second arms having different lengths with the longer arm having a notch formed on its inside edge for receiving the tip of the shorter arm when the first and second arms are brought toward each other by the bias device.

16. The syringe plunger driver system of claim 15 wherein the first and second arms are curved inwardly, whereby the first and second arms are adapted to capture syringe plunger flanges of different sizes.

17. The syringe plunger driver system of claim 1 wherein the bias device comprises a spring connected with the plunger retainer that biases the arms pivotally inward towards each other, the spring having enough force to retain a plunger flange in between the arms during the operation mode.

18. The syringe plunger driver system of claim 1 wherein the arms are asymmetric.

19. A syringe plunger driver system for engaging syringe plungers of different sizes, each plunger having a plunger piston, a plunger flange having an outer diameter, and a plunger stem interconnecting the piston with the flange, and each plunger forming a part of a syringe, each syringe having a barrel in which the plunger moves, each plunger flange having an inner side facing the syringe barrel and an outer side, the syringe plunger driver system having a plunger driver adapted to move the syringe plunger into the syringe barrel in an operation mode, the syringe plunger driver system comprising:
  a pushing surface located on the plunger driver adapted to press against the outer side of the plunger flange to move the flange toward the barrel during the operation mode wherein the pushing surface has a size that is large enough to engage plunger flanges ranging from relatively small to relatively large outer diameters;
  a plunger retainer located on the plunger driver adapted to capture adjacent the pushing surface of the plunger driver syringe plunger flanges ranging from relatively small to relatively large outer diameters, the plunger retainer comprising:
    a first arm having a first length and an inner edge, the first arm being movably mounted on the plunger driver to engage a plunger flange at a first location thereof;
    a second arm movably mounted on the plunger driver having a second length shorter than the first length of the first arm to engage a plunger flange at a different location than the first arm such that the first and second arms apply force towards each other to the plunger flange to capture the flange;
    wherein the ranges of movement of the first and second arms are selected so that the first and second arms engage plunger flanges ranging from relatively small to relatively large outer diameters and in the operation mode, the plunger retainer having a plurality of operating configurations at least one of which comprises a tip of the second arm contacting the inner edge of the first arm when engaging a plunger flange that is relatively small and a second of which comprises the first and second arms not touching each other when engaging a plunger flange that is relatively large;
    wherein the first and second arms have inside edges facing each other and the first arm comprises a notch on its inside edge for receiving the tip of the second arm and the arms are pivotally mounted to the plunger driver in selected locations such that the bias device will move the tip of the second arm into the notch of the first arm when no flange is present between the first and second arms;
    wherein the inside edge of at least one of the first and second arms comprises an anti-siphon ledge configured to engage the inner side of the plunger flange to restrain the plunger flange from movement toward the syringe barrel; and
  a bias device connected with the first and second arms to bias the arms toward each other to capture the plunger flange between the first and second arms.

20. The syringe plunger driver system of claim 19 further comprising a force detector located in the plunger driver and adapted to sense force exerted by the pushing surface against the plunger flange, the force detector outputting a force signal representative of the force exerted against the plunger flange.

21. The syringe plunger driver system of claim 20 wherein the plunger driver includes a force concentrator that defines the pushing surface, whereby the force exerted against the plunger flange is concentrated on the pushing surface of the force concentrator so that the force detector can accurately sense the force exerted.

22. A syringe plunger driver system for engaging syringe plungers of different sizes, each plunger having a plunger piston, a plunger flange having an outer diameter, and a plunger stem interconnecting the piston with the flange, and each plunger forming a part of a syringe, each syringe having a barrel in which the plunger moves, each plunger flange having an inner side facing the syringe barrel and an outer side, the syringe plunger driver system having a plunger driver adapted to move the syringe plunger into the syringe barrel in an operation mode, the syringe plunger driver system comprising:
  a pushing surface located on the plunger driver adapted to press against the outer side of the plunger flange to move the flange toward the barrel during the operation mode wherein the pushing surface has a size that is large enough to engage plunger flanges ranging from relatively small to relatively large outer diameters;
  a plunger retainer located on the plunger driver adapted to capture adjacent the pushing surface of the plunger driver syringe plunger flanges ranging from relatively small to relatively large outer diameters, the plunger retainer comprising:
    a first arm having a first length and an inner edge, the first arm being movably mounted on the plunger driver to engage a plunger flange at a first location thereof;
    a second arm movably mounted on the plunger driver having a second length shorter than the first length of the first arm to engage a plunger flange at a different location than the first arm such that the first and second arms apply force towards each other to the plunger flange to capture the flange;

wherein the ranges of movement of the first and second arms are selected so that the first and second arms engage plunger flanges ranging from relatively small to relatively large outer diameters and in the operation mode, the plunger retainer having a plurality of operating configurations at least one of which comprises a tip of the second arm contacting the inner edge of the first arm when engaging a plunger flange that is relatively small and a second of which comprises the first and second arms not touching each other when engaging a plunger flange that is relatively large;

wherein the first and second arms have inside edges facing each other and the first arm comprises a notch on its inside edge for receiving the tip of the second arm and the arms are pivotally mounted to the plunger driver in selected locations such that the bias device will move the tip of the second arm into the notch of the first arm when no flange is present between the first and second arms;

wherein the inside edge of at least one of the first and second arms comprises an anti-siphon ledge configured to engage the inner side of the plunger flange to restrain the plunger flange from movement toward the syringe barrel;

wherein the first and second arms are curved inwardly, whereby the first and second arms are adapted to capture syringe plunger flanges of different sizes; and a bias device connected with the first and second arms to bias the arms toward each other to capture the plunger flange between the first and second arms.

23. The syringe plunger driver system of claim 22 further comprising a force detector located in the plunger driver and adapted to sense force exerted by the pushing surface against the plunger flange, the force detector outputting a force signal representative of the force exerted against the plunger flange.

24. The syringe plunger driver system of claim 23 wherein the plunger driver includes a force concentrator that defines the pushing surface, whereby the force exerted against the plunger flange is concentrated on the pushing surface of the force concentrator so that the force detector can accurately sense the force exerted.

25. A syringe plunger driver system for engaging syringe plungers of different sizes, each plunger having a plunger piston, a plunger flange, and a plunger stem interconnecting the piston with the flange, and each plunger forming a part of a syringe, each syringe having a barrel in which the plunger moves, each plunger flange having an inner side facing the syringe barrel and an outer side, the syringe plunger driver system having a plunger driver adapted to move the syringe plunger into the syringe barrel in an operation mode, the syringe plunger driver system comprising:

a pushing surface located on the plunger driver adapted to press against the outer side of the plunger flange to move the flange toward the barrel during the operation mode;

a plunger retainer located on the plunger driver adapted to capture the plunger of the syringe, the plunger retainer comprising:

a first arm mounted on the plunger driver; and a second arm mounted on the plunger driver at a location spaced-apart from the first arm, said first and second arms being asymmetric;

a bias device connected with the first and second arms to bias the arms toward each other to capture the plunger flange between the first and second arms; and a control device mounted to a front surface of the plunger driver and interconnected with the first and second arms, the front surface being perpendicular to the pushing surface, the control device including a rotation knob comprising an exposed surface for manual manipulation, the rotation knob having a first rotation position at which the knob moves the first and second arms outwardly into a syringe plunger non-engagement position in opposition to the bias device, and a second rotation position at which the knob does not prevent the first and second arms from capturing the syringe plunger flange;

wherein rotational movement of the rotation knob is substantially parallel to the front surface.

26. The syringe plunger driver system of claim 25 wherein the exposed surface being substantially parallel to the pushing surface when the rotation knob is in the first rotation position, thereby permitting the rotation knob to be used as a handle for moving the pushing surface so that it presses against the outer side of the plunger flange, and the exposed surface being non-parallel to the pushing surface when the rotation knob is in the second rotation position.

27. The syringe plunger driver system of claim 25 wherein the control knob comprises a raised flange for manual maniipulation of the control knob.

* * * * *